US010070985B2

(12) United States Patent
Glazener et al.

(10) Patent No.: US 10,070,985 B2
(45) Date of Patent: Sep. 11, 2018

(54) CERVICAL SPINE ORTHOSIS (71) Applicant: The Methodist Hospital System, Houston, TX (US)

(72) Inventors: Pamela Gail Glazener, Pearland, TX (US); Tom Dibello, Friendswood, TX (US); Richard Neider, Missouri City, MO (US); Jim Flemming, Rosenburg, TX (US)

(73) Assignee: The Methodist Hospital System, Houston, TX (US)

( * ) Notice: Subject to any disclaimer, the term of this patent is extended or adjusted under 35 U.S.C. 154(b) by 235 days.

(21) Appl. No.: 14/378,865

(22) PCT Filed: Feb. 14, 2013

(86) PCT No.: PCT/US2013/026210
§ 371 (c)(1),
(2) Date: Aug. 14, 2014

(87) PCT Pub. No.: WO2013/123246
PCT Pub. Date: Aug. 22, 2013

(65) Prior Publication Data
US 2015/0202072 A1 Jul. 23, 2015

Related U.S. Application Data

(60) Provisional application No. 61/598,687, filed on Feb. 14, 2012.

(51) Int. Cl.
*A61F 5/05* (2006.01)
*A61F 5/058* (2006.01)
*A61F 5/02* (2006.01)

(52) U.S. Cl.
CPC ............ *A61F 5/05883* (2013.01); *A61F 5/02* (2013.01)

(58) Field of Classification Search
CPC .... A61F 5/02; A61F 5/026; A61F 5/05; A61F 5/055; A61F 5/058; A61F 5/05883; A61F 5/0102; A61F 5/05808; A61F 5/3707
See application file for complete search history.

(56) References Cited

U.S. PATENT DOCUMENTS 4,593,788 A * 6/1986 Miller ................. A61F 5/05883
128/869
5,242,377 A * 9/1993 Boughner ............... A61F 5/055
602/17

(Continued)

OTHER PUBLICATIONS

International Search Report issued in related International Application No. PCT/US2013/026210, dated Jun. 2, 2013.

(Continued)

*Primary Examiner* — Tarla Patel
(74) *Attorney, Agent, or Firm* — Meunier Carlin & Curfman LLC (57) ABSTRACT

Implementations of the present disclosure overcome the problems of the prior art by providing a brace for supporting a head of a wearer. The brace includes a head frame, a strap assembly and a cervical bar. The head frame is configured to grip the head of the wearer. The strap assembly is configured to extend along the wearers waist and back. The cervical bar has a first and second ends. The first end connects to and supports the head frame. The second end connects to and is supported by the strap assembly. Advantageously, the cervical bar has a stiffness sufficient to support the head and the head frame against head drop. The brace can do this without interfering with respiratory pathways.

15 Claims, 14 Drawing Sheets

(56) References Cited

U.S. PATENT DOCUMENTS

| | | | | |
|---|---|---|---|---|
| 5,411,471 | A | * | 5/1995 | Terrazas .................. A61F 5/055 |
| | | | | 2/421 |
| 6,267,741 | B1 | * | 7/2001 | Lerman .................. A61F 5/055 |
| | | | | 128/DIG. 23 |
| 2005/0245854 | A1 | * | 11/2005 | Leuthardt ............... A61F 5/055 |
| | | | | 602/18 |
| 2010/0204628 | A1 | * | 8/2010 | Ghajar .................... A61F 5/055 |
| | | | | 602/18 |
| 2010/0318010 | A1 | * | 12/2010 | Sandifer ................. A61F 5/026 |
| | | | | 602/19 |

OTHER PUBLICATIONS

Dynamic Cervical Orthosis Prefab Instructions published by SURESTEP, 2015, accessed on Jan. 30, 2018, at http://surestep.net/wp-content/uploads/2017/05/DCO-Instructions-2015_PreFab.pdf.

Dynamic Cervical Orthosis Custom Instructions published by SURESTEP, 2015, accessed on Jan. 30, 2018, at http://surestep.net/wp-content/uploads/2017/05/DCO-Instructions-2015_Custom.pdf.

Dynamic Cervical Orothosis Order Form published by SURESTEP, Jul. 2017, accessed on Jan. 30, 2018, at http://surestep.net/wp-content/uploads/2017/09/OTS_Order_Forms_DCO_July2017.pdf.

Dynamic Cervical Orothosis Brochure issued by SURESTEP, 2017, accessed on Jan. 30, 2018, at http://surestep.net/wp-content/uploads/2017/05/DCO-Brochure-1.pdf.

Dynamic Cervical Orthosis, http://surestep.net/products/dynamic-cervical-orthosis/, 2017, accessed on Jan. 30, 2018.

\* cited by examiner

CERVICAL SPINE ORTHOSIS

CROSS REFERENCE TO RELATED APPLICATIONS

This application claims the benefit of priority to U.S. Provisional Application 61/598,687, filed Feb. 14, 2012, which is incorporated by reference herein in its entirety.

FIELD OF THE INVENTION

The invention pertains to a brace for providing support to the head and torso of the wearer without the use of a cervical collar, thereby improving the wearer's balance, mobility, and breathing capacity.

BACKGROUND

Amyotrophic lateral sclerosis (ALS), also known as Lou Gehrig's disease, is a progressive neurodegenerative disease which leads to muscular weakness. This disease causes a deterioration of upper and lower motor neurons which can result in a variety of deficits including weakness, speech difficulty, swallowing difficulty, spasticity, weight loss, muscle atrophy, shortness of breath, fatigue and eventually respiratory failure.

There is no known cause or cure for ALS. One of the muscle groups frequently affected with weakness and fatigue are the neck extensors. Due to this weakness, individuals lose the ability to control one's head even though they may continue to be independent with ambulation.

Many people with ALS who exhibit neck extensor weakness, find it difficult to ambulate due to the flexed neck position. This flexed neck position impacts the person's ability to breathe, causes unstable balance, fatigue, pain and ultimately poor quality of life.

People with neck weakness (due to ALS and other reasons) may rely on external supports for head control. Such supports include neck braces or high back wheelchairs with head supports. Multiple cervical collars are available on the market, including the Aspen collars, Head master collars, non-invasive halo, Minerva brace, SOMI brace and the MND Oxford collar. The current external supports rely upon posterior support, anterior chin support and an optional chest or back strap or plate.

It would be advantageous to have a cervical spine orthosis that further improves the quality of life, balance, mobility and breathing capacity of people with ALS and other diseases.

SUMMARY

Implementations of the present disclosure overcome the problems of the prior art by providing a brace for supporting a head of a wearer. The brace includes a head frame, a strap assembly and a cervical bar. The head frame is configured to grip the head of the wearer. The strap assembly is configured to extend along the wearer's waist and back. The cervical bar has a first and second ends. The first end connects to and supports the head frame. The second end connects to and is supported by the strap assembly. Advantageously, the cervical bar has a stiffness sufficient to support the head and the head frame against head drop. The brace can do this without interfering with respiratory pathways.

The strap assembly includes at least one waist strap configured to extend at least partially around a waist of the wearer. Also included may be a posterior panel. The posterior panel may be configured to extend along a wearer's back. The posterior panel has a first end and a second end. The first end of the posterior panel is connected to the second end of the cervical bar. The second end of the posterior panel is connected to the waist strap. The posterior panel may be relatively stiff to provide additional support.

The strap assembly may include shoulder straps. Each of the shoulder straps has a first end and a second end. The first end of the shoulder strap is connected to the first end of the posterior panel. The second end of the shoulder strap is connected to the waist strap.

Also, the strap assembly may include an anterior panel constructed of a relatively stiff material. The anterior panel is configured to extend across a portion of the wearer's abdomen. The waist strap is connected to the anterior panel.

To avoid interference with respiration, the brace may be configured to have a free area under the chin and over the chest of the wearer. The brace may be configured to be relatively free of rigid structure near a respiratory pathway of the wearer.

The head frame may include a posterior portion including a stiff material having a concave shape with lateral extensions. The lateral extensions are configured to extend along lateral sides of the wearer's head.

Also, the head frame may include a head strap configured to extend around a forehead of the wearer and couple to the posterior portion.

A method of supporting a head of a patient using a brace. The head frame is positioned on the head of the patient. The head frame is secured to a first end of a cervical bar, where the second end of the cervical bar is secured to a posterior panel. The posterior panel is secured to the patient's torso. These steps may be executed while avoiding interference with respiration of the wearer. For example, the chin and chest area may be avoided.

These and other features and advantages of the implementations of the present disclosure will become more readily apparent to those skilled in the art upon consideration of the following detailed description and accompanying drawings, which describe both the preferred and alternative implementations of the present disclosure.

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

As shown in FIGS. 1-5, a brace 10 includes a head frame 12, a cervical bar 14, a posterior panel 20, shoulder straps 16, waist straps 22 and an anterior panel 24. The head frame 12 is configured to grip the head of the wearer. The strap assembly, such as the shoulder straps 16, waist straps 22, posterior panel 20 and anterior panel 24, provide a secure foundation for the head frame 12 without interfering with respiration. The cervical bar 14 is relatively stiff and connects the head frame 12 to the strapping system so as to support the wearer's head. This helps to mitigate the "head drop" in ALS patients and other patients afflicted with neck instability or insufficiency.

Figure 4:
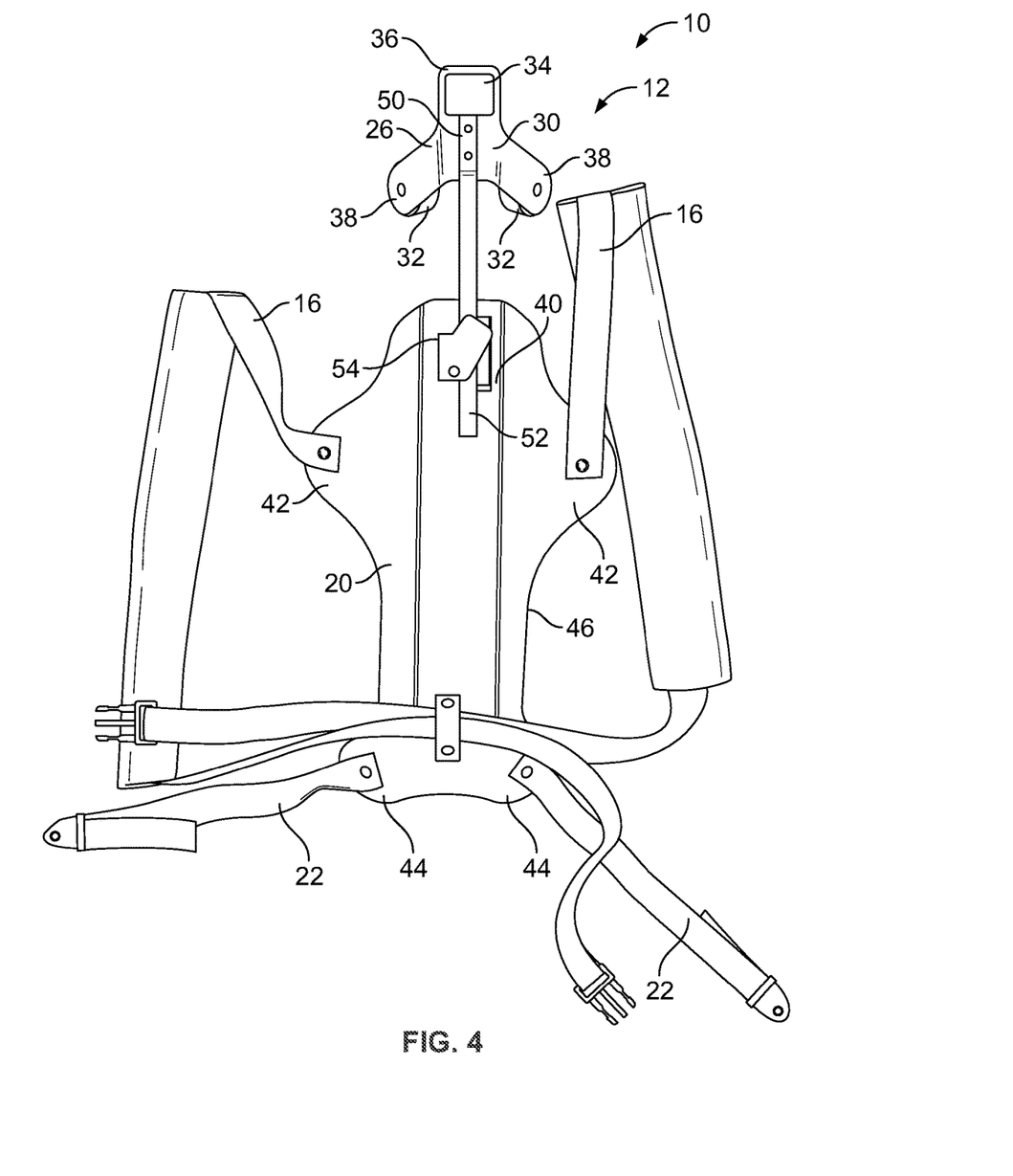
FIG. 4 is a rear plan view of the example brace of FIG. 1.
Figure 5:
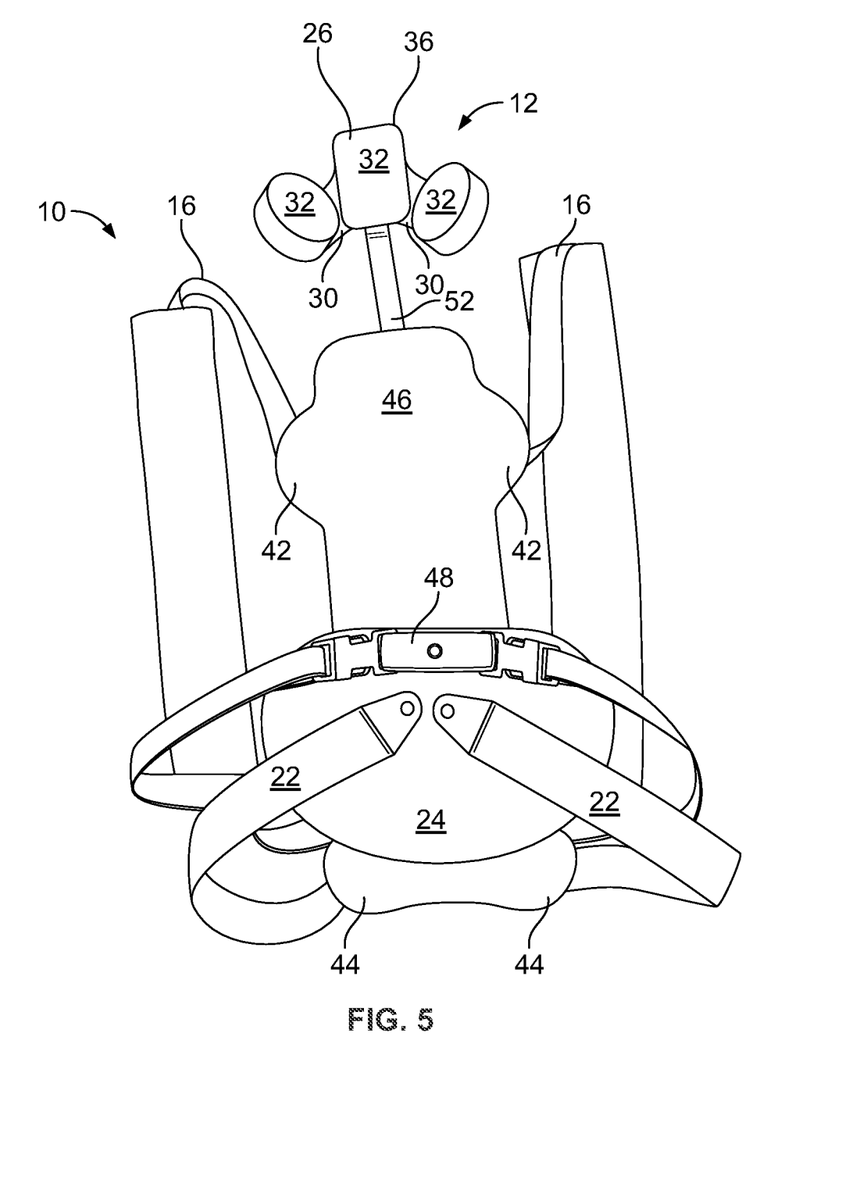
FIG. 5 is a front plan view of the example brace of FIG. 1.

As shown in FIGS. 4 and 5, the head frame 12 includes a posterior portion 26 and a head strap 28. The posterior portion 26 includes a frame member 30, padding 32 and a hook and loop panel 34. The frame member 30 is formed of a relatively stiff sheet of material, such as from a 4 inch by 6 inch blank of 1/16 of an inch thick T3 aluminum sheet for smaller wearers or a 5 inch by 7 inch blank for larger wearers.

Figure 1:
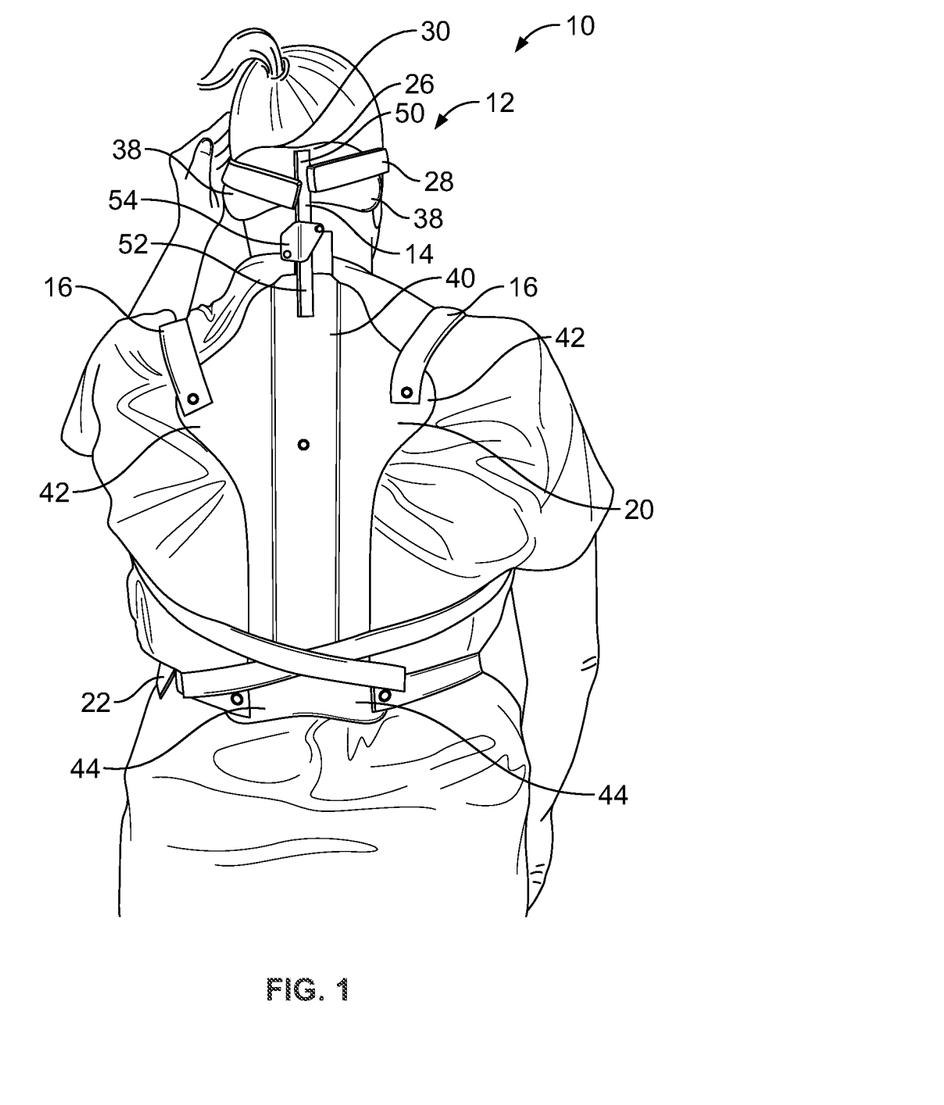
FIG. 1 is a rear elevation view of an example brace worn by a wearer.
Figure 9:
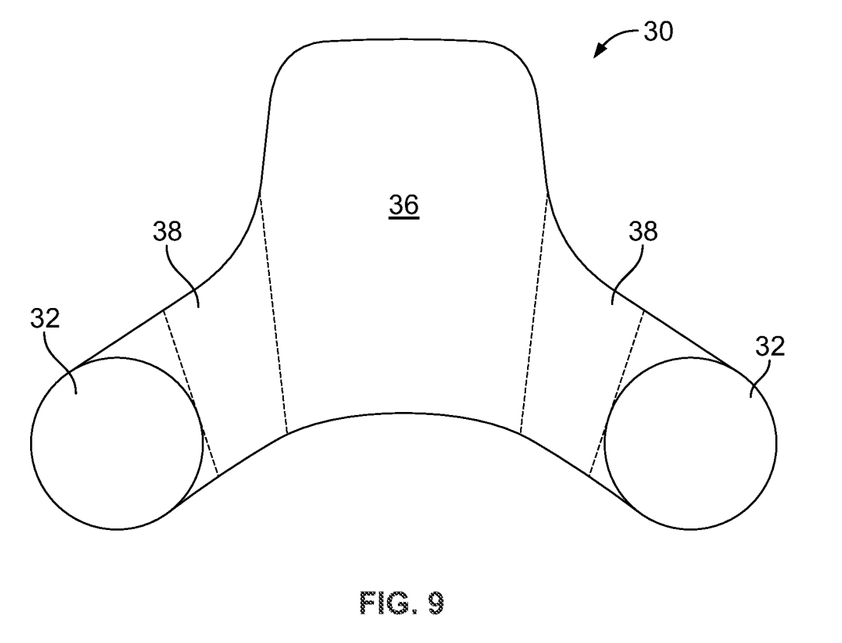
FIG. 9 is a plan view of an example blank used to form a frame member.

An exemplary flat frame member 30 formed from such a blank is shown in FIG. 9 and includes a central rectangular portion 36 and a pair of lateral extensions 38. Broken lines in FIG. 9 show where the lateral extensions 38 can be bent into the concave shape shown in FIGS. 3, 4 and 5. The central rectangular portion 36 has a slight arc curvature at its bottom edge and a relatively straight top edge. The central rectangular portion 36 is longer than it is wide and is configured to extend up along the posterior portion of the base of the wearer's head, as shown in FIG. 1.

Figure 10:
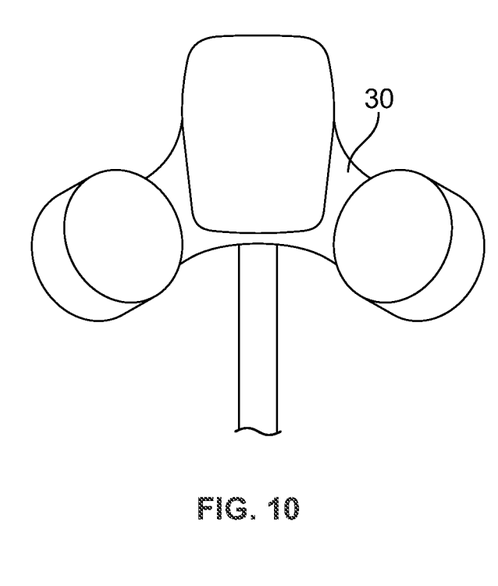
FIG. 10 is a front plan view of an example head frame.
Figure 11:
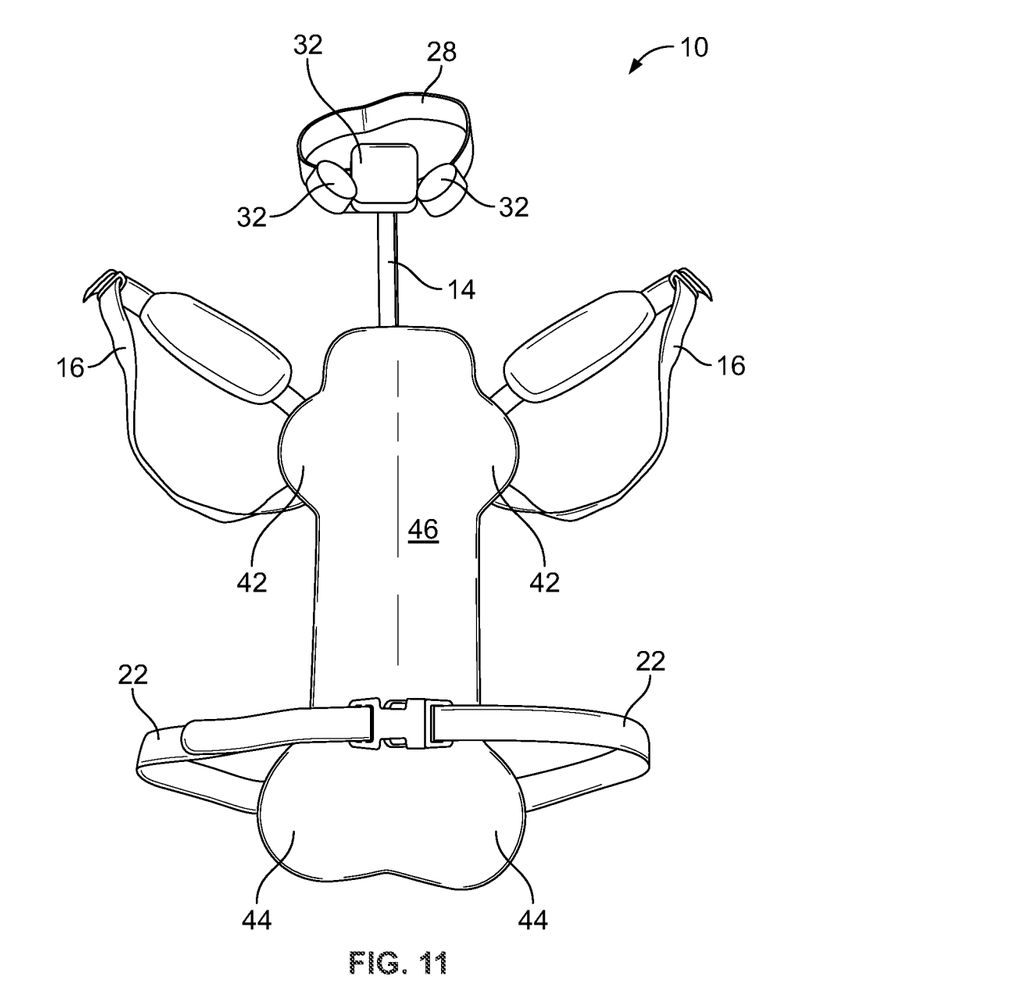
FIG. 11 is a front plan view of an example brace.

That lateral extensions 38 are rounded lobes of the stiff sheet material that extend slightly downwards away from the central rectangular portion 36. As illustrated in FIG. 10, the lateral extensions 38 can be bent inwards to form the aforementioned concave shape, about 30 to 45 total degrees from the plane of the central rectangular portion 36. The 45 degrees, for example, may comprise a 20 degree bend at the more medial (inner) broken lines of lateral extensions 38. The remaining 25 degree bend is at the more lateral (outer) broken lines of the lateral extensions. Despite the initial curvature of the head frame member 30, it may be contoured to match the wearer's anatomy for a snug comfortable fit and prevent slippage off of the occiput.

Because the broken lines along which the bends are made are closer at the bottom than the top, the inside surfaces of the lateral extensions 38 are angled slightly upwards to extend along the occipital lobe and toward the center of the wearer's head. Together, the central rectangular portion 36 and lateral extensions 38 form support surfaces with a net vector directed anteriorly and superiorly to tilt the head held thereagainst by the head strap 28 into a more normal anatomical position.

Figure 6:
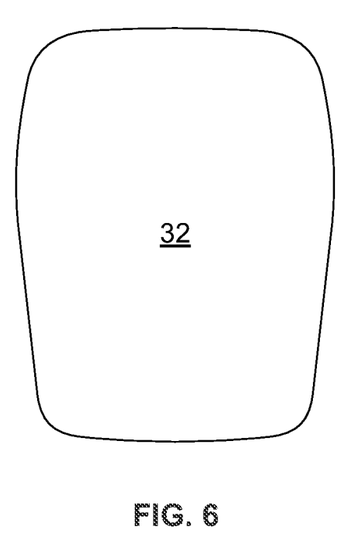
FIG. 6 is a front view of an example occipital pad.
Figure 7:
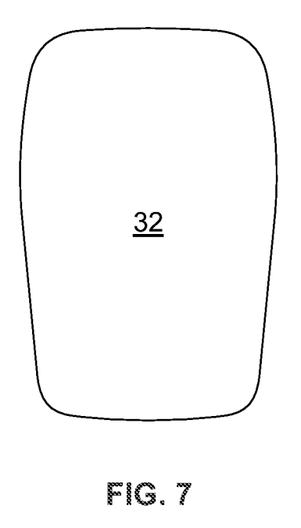
FIG. 7 is a front view of an example occipital pad.
Figure 8:
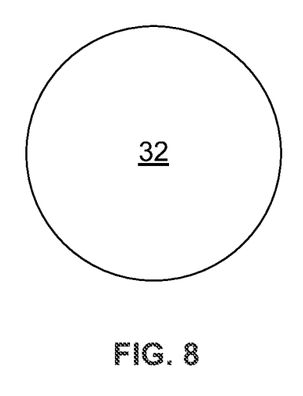
FIG. 8 is a front view of an example occipital pad.

Wearer comfort is facilitated by use of padding 32 applied to the frame member 30, as shown in FIGS. 5 and 10. Padding 32 includes a rectangular occipital pad for larger wearers, such as is shown in FIG. 6, or a smaller rectangular pad for smaller wearers, as shown in FIG. 7. Also, circular occipital pads, as shown in FIG. 8, are used for the lateral extensions 38. The padding 32 may be constructed of 1/4 inch VOLARA foam or 1/2 inch PLASTAZOTE foam. The smaller (by diameter) lateral occipital pads may be constructed of the thicker foam for more conforming support. The foam padding 32 may be attached by adhesive or fasteners to the allotted positions on the frame member 30.

The hook and loop panel 34 is a rectangular panel adhered to the upper outside surface of the central rectangular portion 36, as shown in FIG. 4. The hook and loop panel can include, for example 1 inch wide by 20 inch long 50/50 Hook & Loop, a 1½ inch pressure sensitive hook, and a 1 inch C-loop. This optional panel provides additional security for the loop (or hook) bearing head band or strap 28.

Figure 2:
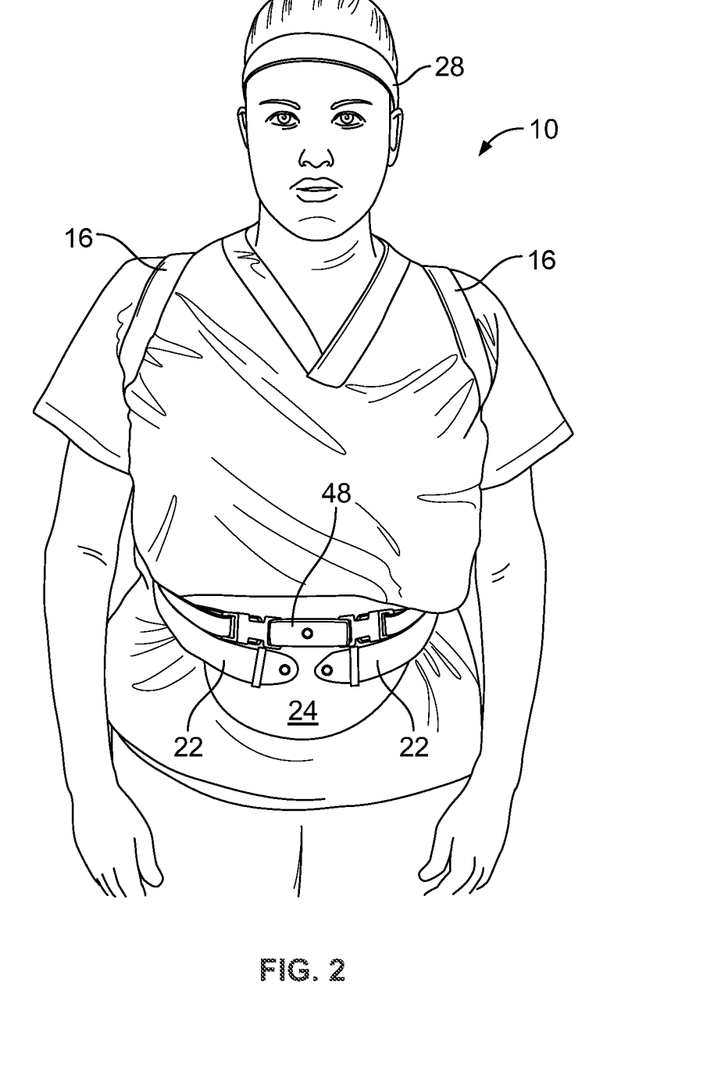
FIG. 2 is a front view of the example brace of FIG. 1.
Figure 3:
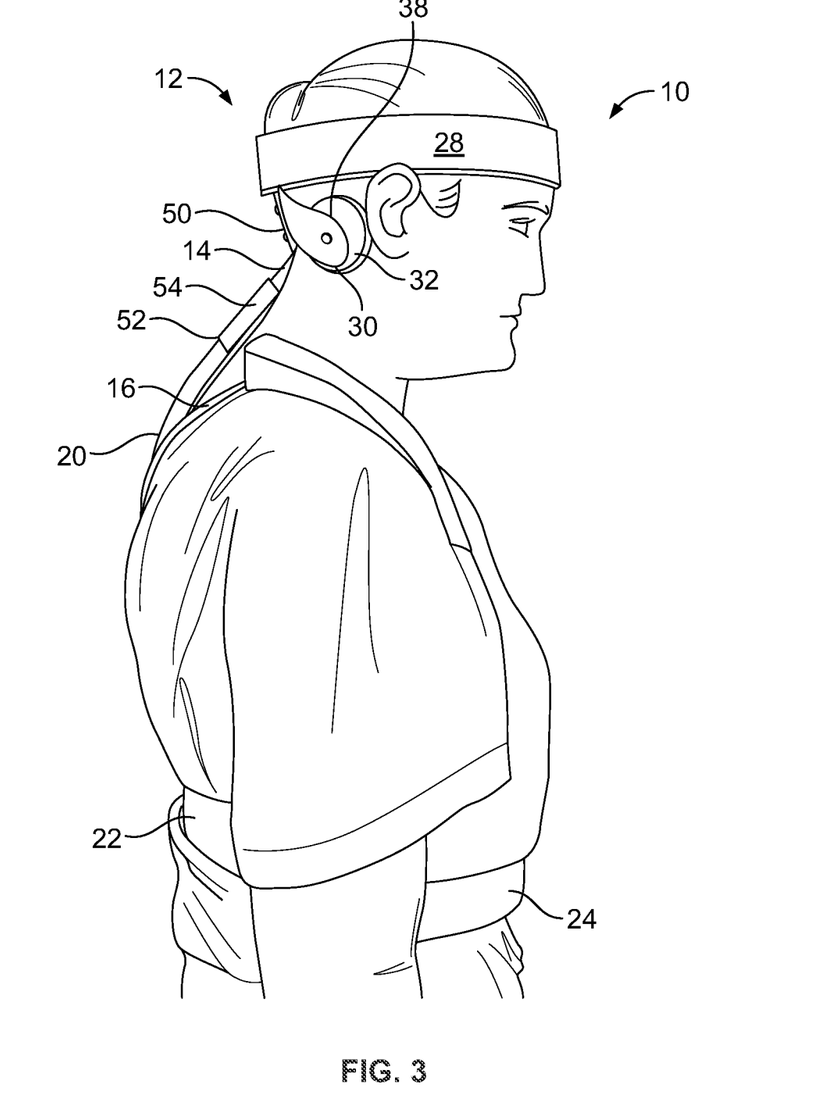
FIG. 3 is a side view of the example brace of FIG. 1.

The head strap 28 extends in a loop around the forehead of the wearer, as shown in FIGS. 2 and 3. The head strap 28 thus secures the head to, and within, the upwardly extended concave receptacle formed by the frame member 30. The head strap 28 may be formed of 1/8 inch thick by 1½ inch wide by 5 inch long neoprene strip, such as NEO-SPONGE, attached (e.g., sewn or adhered) to a 1 inch DACRON strap.

The strap assembly includes the shoulder straps 16, waist straps 22, posterior panel 20 and anterior panel 24. The posterior panel 20, as shown in FIG. 4, is formed of a curved sheet of relatively stiff material, such as a 2 foot by 3 foot by 3/16 inch thick polypropylene sheet. The posterior panel 20 has an elongate shape and extends from the neck to the waist of the wearer. It is curved to match the kyphotic curve of the thoracic spine of the wearer. Embedded within or attached to the polypropylene sheet may be a central reinforcing strut or bar 40 for additional rigidity. The strut 40 may be constructed, for example, of a 2 inch wide, 19 inch long and 1/8 inch thickness T4 aluminum bar. The strut 40 may be inserted, attached or formed into the posterior panel 20.

The posterior panel 20 also includes shoulder flanges 42, waist flanges 44 and a foam layer 46, as shown in FIG. 5. The shoulder flanges 42 and waist flanges 44 are shaped or cut from the sheet of polypropylene. For example, the posterior panel 20 can be constructed from 1/8 inch KYDEX 430 plastic. The shoulder flanges 42 extend laterally at shoulder height from the central portion of the posterior panel 20. They are configured to accept attachment of the shoulder straps 16. The waist flanges 44 similarly extend laterally at waist level from the central portion. They are configured to accept attachment of the waist straps 22. The foam layer 46 may be 1/4 inch ALIPLAST foam cut to the shape of the overall posterior panel 20, a shown in FIG. 5.

As shown in FIG. 4, the shoulder straps 16 include 1 inch DACRON straps with 1/4 inch VELFOAM sheets wrapped into sleeves surrounding the DACRON straps. A first end of each of the shoulder straps 16 connects by fastener to a respective one of the shoulder flanges 42. A second end of each one of the shoulder straps ends in a 1 inch double adjustable side release buckle. The intervening length of the DACRON strap extends through a loop attached to posterior panel 20 between the two waist flanges 44. At this point, the shoulder straps cross each other to extend back out and around the waist of the wearer to buckle to the anterior panel 24, as shown in FIG. 1.

The waist straps 22 connect at a first end to the waist flanges 44 via fasteners and are configured to extend around the waist and/or hips of the wearer to attach at a second end (also via fasteners) to the anterior panel 24. The second ends each include an adjustable buckle or ring (such as a D-ring). The waist straps 22 may be constructed of 2 inch DACRON straps that extend through the ring and then double-back to attach (adjustably) to themselves with an intervening hook-and-loop connector strip.

The anterior panel 24, as shown in FIGS. 2 and 5, is a D-shaped panel with a flat top, arc-shaped bottom and rounded corners configured for positioning over the abdominal region of the wearer. It includes a waist strap connector 48 that is anchored at its center and its ends include mating buckle portions configured to mate with buckles on the free ends of the shoulder straps 16. It is also constructed of a relatively stiff or rigid material.

The cervical bar 14 includes a first end 50 and a second end 52 separated by a bend in the bar. The cervical bar 14 may be constructed of a ⅛ inch thick by ⅝ thick by 9½ long 2024 T4 aluminum bar. The cervical bar 14 can be adjusted to correspond to the curvature of the trunk of the wearer. For example, the height of the cervical bar 14 can be adjusted with respect to the posterior panel 20. The first end 50 rigidly attaches via two fasteners to the rectangular portion 36 of the frame member 30. The second end 52 extends over and attaches to the top of the reinforcing strip 40 of the posterior panel 20.

Figure 15:
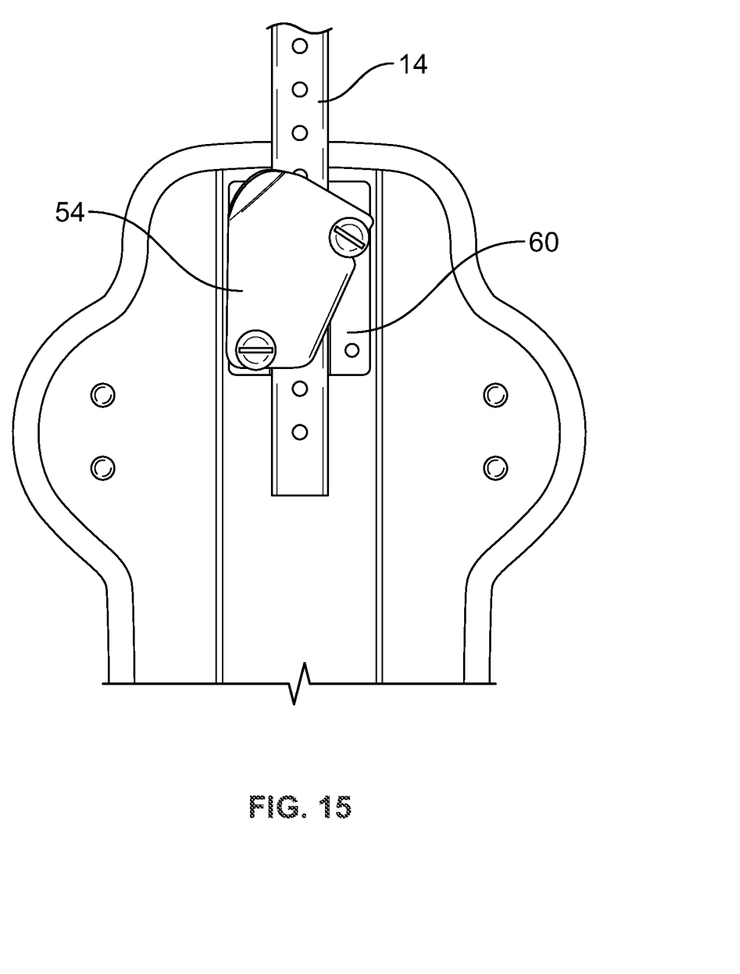
FIG. 15 is a front plan view of an example connector.
Figure 16:
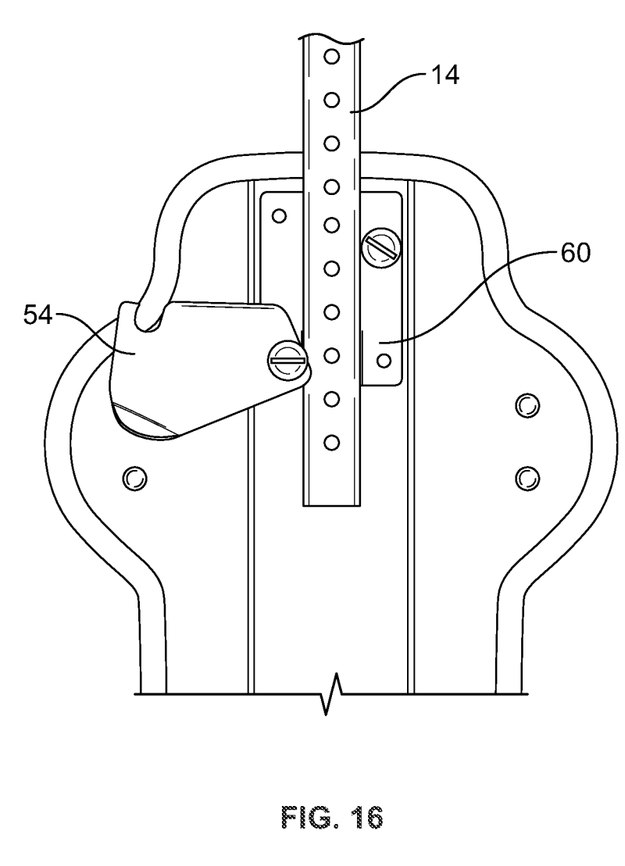
FIG. 16 is a front plan view of an example connector.
Figure 17:
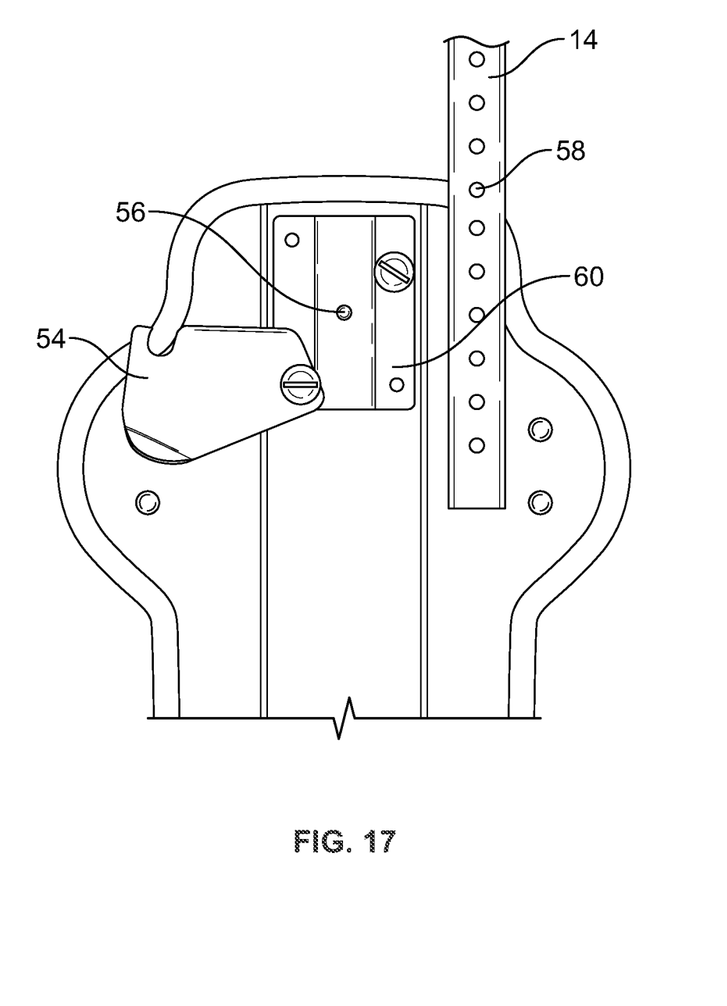
FIG. 17 is a front plan view of an example connector.

The posterior panel 20 may include a slot that receives the second end 52. The posterior panel 20 may include an adjustable connector 60 for coupling with the second end 52. For example, as illustrated in FIGS. 15-17, the connector 60 can include a pin 56 or other fastener may be used to extend into one of series of vertically spaced openings 58 defined in the second end 52 of the cervical bar 14. The connector 60 allows the height of the head frame 12 to be adjusted relative to the posterior panel 20. FIG. 15 shows the cervical bar 14 in an engaged or locked position with respect to the posterior panel 20. The cover plate 54 can be positioned over the connector 60 using a mechanical fastener. FIG. 16 shows the connector 60 with the cover plate 54 open and the cervical bar 14 positioned/engaged within the connector 60. The cover plate 54 can rotate/pivot at a screw/pin from an open to closed position over the connector 60. FIG. 17 shows the cover plate 54 in an open position and the cervical bar 14 removed from the connector 60. As illustrated in FIG. 17, an example connector can include a pin 56 integral to the connector 60 for engaging the openings 58 defined in the second end of the cervical bar 14. In a further example the pin 56 may extend from the cover plate 54 and can be selectively detached and reattached (e.g., via screws) to adjust the head frame 12 for different wearers. In another example, the pin 56 can be removably coupled to the cover plate 54 and/or connector 60.

As shown in FIG. 3, the bend in the cervical bar 14 is positioned to transition between the neck and the tilt for the occipital portion of the wearer's skull.

The brace 10 may be donned by positioning the posterior panel 20 along the spine. The wearer places both arms through the shoulder straps 16. The wearer secures the waist straps 22 and anterior panel 24 around their waist using the buckles. The wearer places the posterior portion 26 of the head frame 12 at the lower portion of the head. The wearer secures the head frame 12 against the base of their skull with the head strap 28. If needed, the wearer may readjust the waist straps 22 and anterior panel 24 for improved fit. The wearer may also adjust the shoulder straps 16 to be snug with the hook-and-loop connector.

Advantageously, the brace 10 positions the head in neutral or slight flexion without chin support. The brace 10 includes adjustability to adapt to different wearer physiology. Stabilization of the brace 10 posteriorly with anterior strap components extending around the waist leaves the chest, chin and throat area free for easier respiration. The anterior panel 24 may also have diaphragm assist function that facilitates breathing. The brace 10 may be worn over an undershirt to reduce chafing but under regular clothing for a more acceptable appearance. Experimental wearers of the brace 10 reported satisfaction with comfort, mobility, and ability to breathe more easily than prior art braces.

In a further example, as shown in FIGS. 11-14, the strap assembly includes shoulder straps 16, waist straps 22 and the posterior panel 20, and does not include the anterior panel 24. Shoulder flanges 42 extend laterally at shoulder height from the central portion of the posterior panel 20 and are configured to accept attachment of the shoulder straps 16. The waist flanges 44 similarly extend laterally at waist level from the central portion and are configured to accept attachment of the waist straps 22.

Figure 12:
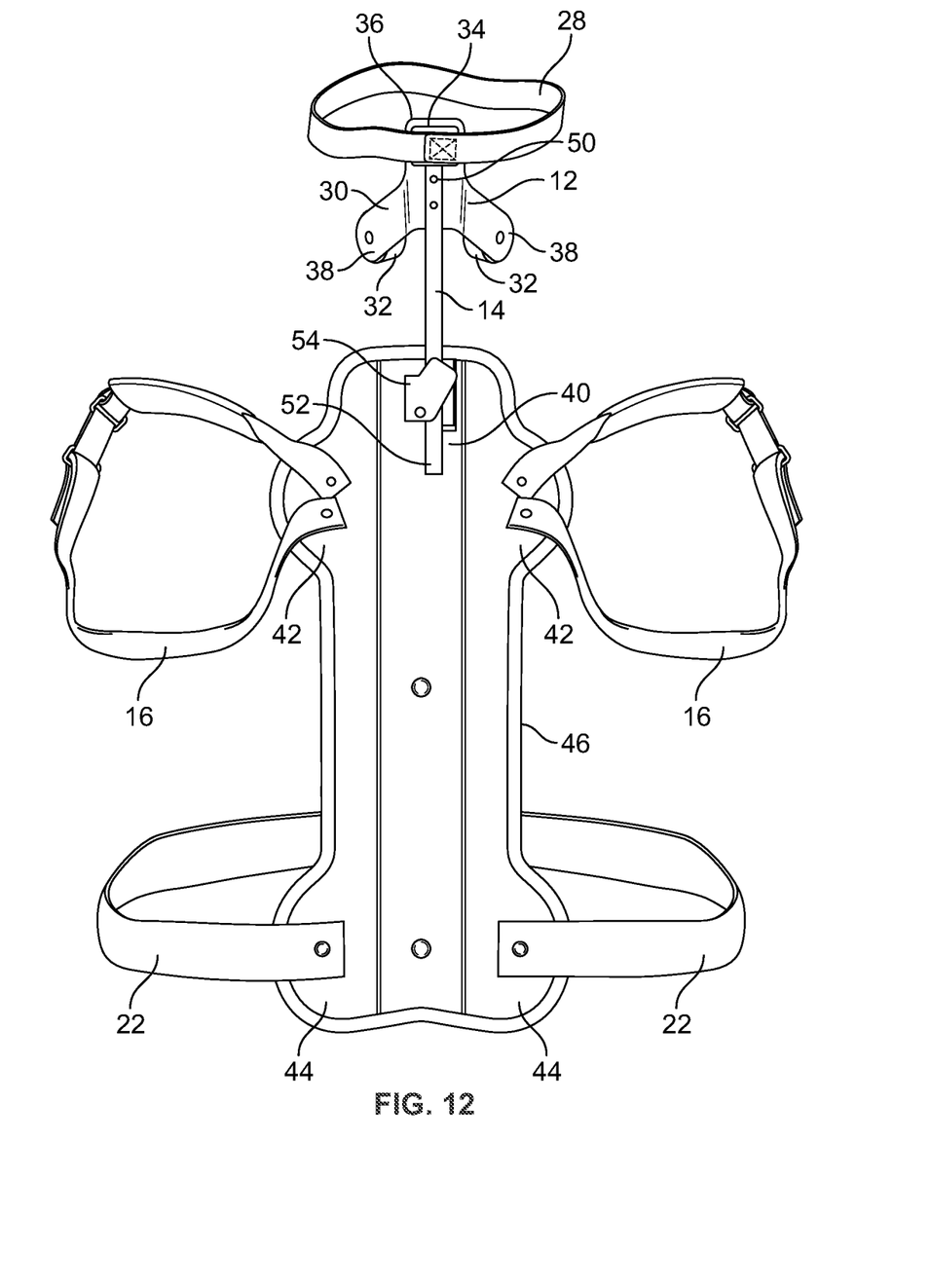
FIG. 12 is a rear plan view of the example brace of FIG. 11.
Figure 13:
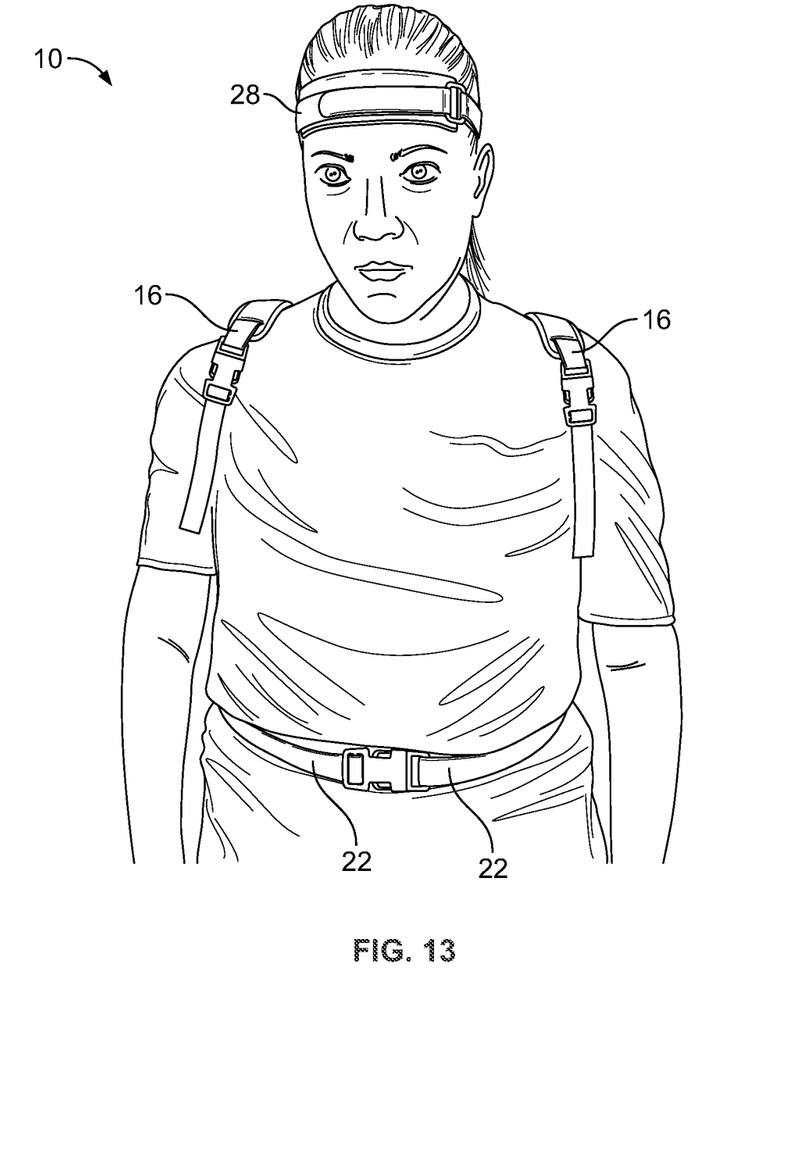
FIG. 13 is a front elevation view of the example brace of FIG. 11 worn by a wearer.
Figure 14:
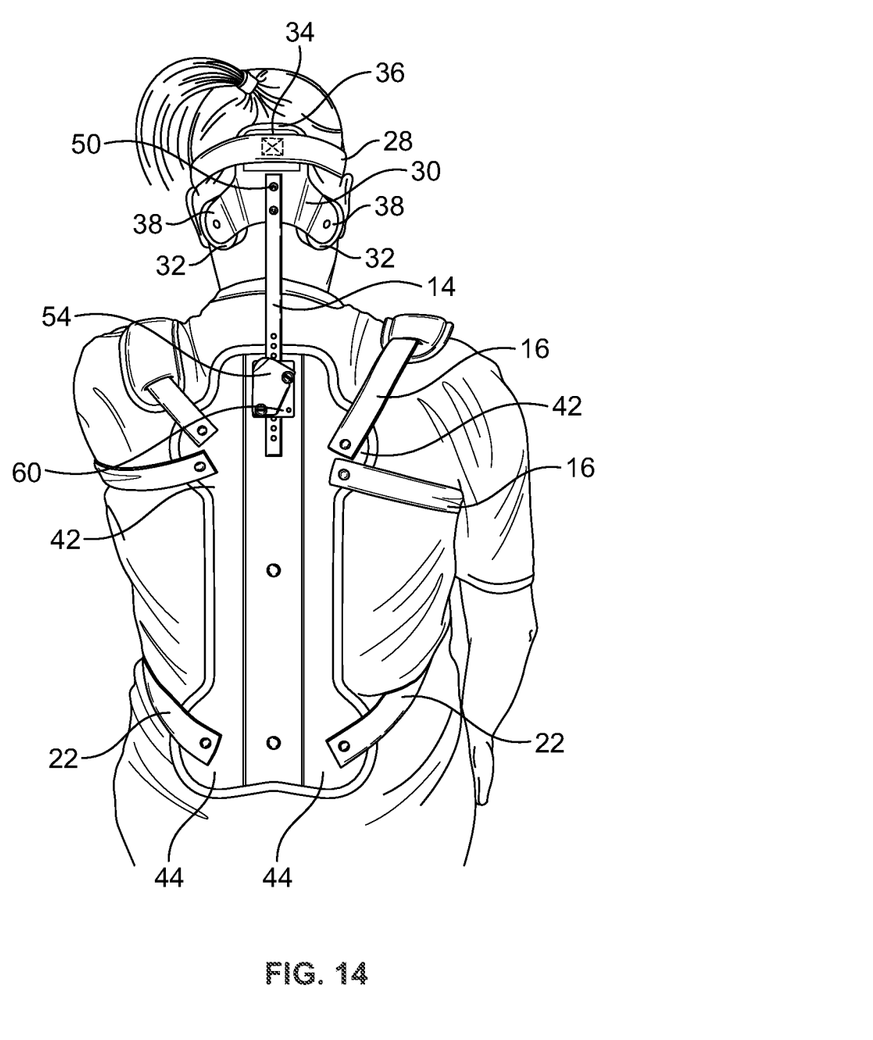
FIG. 14 is a front elevation view of the example brace of FIG. 11 worn by a wearer.

As shown in FIG. 12, each shoulder strap 16 includes a top and bottom segment. One end of the each of the top and bottom segments connects by fastener to a shoulder flange 42. The top and bottom segments mate/join at an adjustable buckle or ring (such as a D-ring) such that the intervening length of the joined shoulder straps 16 extends through left and right side loops attached to the left and right shoulder flanges 42, respectively. The shoulder straps can include a 1 inch double adjustable side release buckle. The shoulder straps 16 can include VELCRO to assist in adjusting/securing the fit around the shoulders of the wearer. For example, shoulder straps 16 can include 1 inch wide by 20 inch long 50/50 Hook & Loop.

A first waist strap 22 connects at a first end to a waist flange 44 via fasteners and a second waist strap 22 connects at a first end to the opposite waist flange 44. The first and second waist straps 22 are configured to extend around the hips of the wearer and mate/join at an adjustable buckle or ring (such as a D-ring). For example, the first and second waist straps 22 can be mated/joined at a 1½ inch double adjustable side release buckle. The first and second waist straps 22 can also include VELCRO to assist in adjusting/securing the fit of the waist straps 22 around the waist/hips of the wearer. For example, waist straps 22 can include 1 inch wide by 20 inch long 50/50 Hook & Loop. In a further example, the brace 10 can be configured such that the first and second waist straps extend around the waist of the wearer. The waist straps 22 may be constructed of 2 inch DACRON straps that extend through the ring and then double-back to attach (adjustably) to themselves with an intervening hook-and-loop connector strip.

The brace 10 may be donned by securing the posterior panel 20 to the torso of the wearer. For example, the posterior panel 20 can be positioned along the wearer's spine and a strapping system can be positioned about the torso of the wearer, including straps around the shoulders, waist and/or hips to securing the posterior panel 20 to the wearer. The strapping system can include waist straps 22 and/or shoulder straps 16. The strapping system can also include an anterior panel 24. The strapping system can be secured to the posterior panel 20 while donning. In another example, end portions of each of the waist straps 22 and/or shoulder straps 16 are fixed to the posterior panel 20 before donning. The fit of the waist straps 22 and/or shoulder straps 16 can be adjusted/secured using buckles, rings, VELCRO, etc.

The head frame 12 can be positioned on the head of the wearer and head straps 28 may be secured around the wearer's head. For example, head straps 28 can be placed across the forehead and around the sides of the wearer's head. The head straps 28 can be fixedly attached to the head frame 12 prior to donning the brace, or the head straps 28 can be secured to the head frame 12 during/after donning the brace. At least a portion of the head frame 12 can be positioned along and/or in contact with the wearer's head. For example, pads 32 attached to the head frame 12 can be positioned such that they come in contact with the wearer's head during use of the brace 10. The head frame 12 can be positioned to support a posterior and/or side portion of the wearer's head. For example, the head frame 12 can be positioned to support at least a portion of the occipital bone. The head frame 12 can be positioned such that it provides support for the weight of the wearer's head. Similarly, the posterior panel 20 can be positioned to provide support for the wearer's torso. For example, the torso/trunk of the wearer can be supported by the leverage provided between the restraint provided at the head frame 12 and the waist straps 22. As the waist straps 22 are tightened against the body of the wearer the posterior panel 20 is brought into contact with at least the lower lumbar portion of wearer's back. The pressure/support provided against the wearer's back combined with the restrain of the wearer's head can position the wearer's torso in an upright position. By supporting the wearer's head and torso, the wearer's balance, walking ability/mobility, and/or breathing can be improved.

The head frame 12 can be secured to a first end 50 of the cervical bar 14. The second end 52 of the cervical bar 14 can be secured to the posterior panel 20. In another example, the second end 52 of the cervical bar 14 can be incorporated into and/or constructed from a portion of the posterior panel 20, in which case the head frame 12 can be secured to the combined posterior panel 20/cervical bar 14.

The wearer can wear regular undergarments under the brace 10. Moreover, regular clothing can be worn over the brace. The brace 10 can be donned without interfering with the respiration of the wearer. For example, because the brace 10 does not include a chin and/or chest strap and can be donned while avoiding the chin and chest areas of the wearer. Likewise, when being worn, the brace 10 does not restrict the ability to breath, eat, and/or speak. The brace 10 can also improve posture and visual orientation by reorienting the location and position of the wearer's head.

A number of aspects of the systems, devices and methods have been described. Nevertheless, it will be understood that various modifications may be made without departing from the spirit and scope of the disclosure. Accordingly, other aspects are within the scope of the following claims.

That which is claimed:

1. A brace for supporting a head of a wearer, the brace comprising:
   a head frame comprising:
      a posterior portion, the posterior portion comprising a central rectangular portion and first and second lateral extensions, the central rectangular portion having a straight upper edge and a lower edge having an arc curvature,
      the first and second lateral extensions extending outwardly from opposite and spaced apart sides of the central rectangular portion, the central rectangular portion and lateral extensions being stiff, the lateral extensions being bendable about the sides of the central rectangular portion toward and concavely around at least a portion of an occipital bone of the wearer's head such that after being bent, the lateral extensions are outside of a plane that includes the central rectangular portion, and
      a head strap coupled to the central rectangular portion, the head strap configured to extend around a forehead of the wearer;
   a posterior panel configured to extend along a back of the wearer; and
   a cervical bar having a first end and a second end, the first end coupled to and supporting the central rectangular portion of the head frame and the second end coupled to and supported by the posterior panel;
   wherein the cervical bar has a stiffness to support the head of the wearer and head frame against head drop.

2. The brace of claim 1, further comprising a strap assembly that includes at least one waist strap configured to extend at least partially around a waist of the wearer.

3. The brace of claim 2, wherein the posterior panel has a first end and a second end, wherein the first end of the posterior panel is connected to the second end of the cervical bar, and the second end of the posterior panel is connected to the at least one waist strap.

4. The brace of claim 3, wherein the posterior panel is a stiff panel.

5. The brace of claim 2, wherein the strap assembly has an anterior panel constructed of a rigid material and configured to extend across a portion of the wearer's abdomen and wherein the at least one waist strap is connected to the anterior panel.

6. The brace of claim 1, wherein the brace is configured to have a free area under a chin of the wearer.

7. The brace of claim 1, wherein the brace is configured to be free of rigid structure near a respiratory pathway of the wearer.

8. The brace of claim 1, wherein the posterior portion includes padding configured to extend between the lateral extensions and the wearer's head.

9. The brace of claim 1, further comprising a strap assembly comprising a waist strap, the waist strap configured to extend around hips of the wearer.

10. The brace of claim 1, further comprising a strap assembly, the strap assembly comprising a right shoulder strap and a left shoulder strap.

11. The brace of claim 10, wherein at least one end of each of the right and left shoulder straps are coupled to the posterior panel.

12. The brace of claim 11, wherein both ends of each right and left shoulder strap are coupled to the posterior panel.

13. The brace of claim 12, wherein the right and left shoulder straps are not coupled to each other anteriorly of the wearer.

14. The brace of claim 13, wherein the strap assembly further comprises at least one waist strap configured to extend at least partially around a waist of the wearer, the waist strap being coupled to the posterior panel.

15. The brace of claim 10, wherein the right and left shoulder straps are not coupled to each other anteriorly of the wearer.

* * * * *